United State
Grolman et al.

[11] 3,947,099
[45] Mar. 30, 1976

[54] SOLID STATE COLOR ANOMALOSCOPE

[75] Inventors: Bernard Grolman, Worcester; Robert G. Lavallee, Ashland, both of Mass.

[73] Assignee: American Optical Corporation, Southbridge, Mass.

[22] Filed: Jan. 2, 1975

[21] Appl. No.: 538,229

[52] U.S. Cl................... 351/35; 350/96 B; 351/36
[51] Int. Cl.[2]........................ A61B 3/06; G02B 5/16
[58] Field of Search ................. 351/35, 36; 357/17; 350/96 B

[56] References Cited
UNITED STATES PATENTS

| | | | |
|---|---|---|---|
| 3,382,025 | 5/1968 | Knoll | 351/35 X |
| 3,489,482 | 1/1970 | Brill | 350/96 B |
| 3,807,838 | 4/1974 | Meyers | 351/35 X |

OTHER PUBLICATIONS

R. W. Pickford et al., *Brit. J. Phys. Optics,* "The Pickford–Nicolson Anomaloscope," Vol. 17, p. 131–150, Dec. 1960.

*Primary Examiner*—Paul A. Sacher
*Attorney, Agent, or Firm*—Howard R. Berkenstock, Jr.; William C. Nealon

[57] ABSTRACT

Apparatus for evaluation a human subject's color vision response including light emmiting diodes providing luminance in the yellow and red and green color spectrums, means for controlling the individual luminescence of the red and green diodes in an inverse relationship and means for displaying the yellow and red-green luminescence for comparative viewing by the human subject.

4 Claims, 2 Drawing Figures

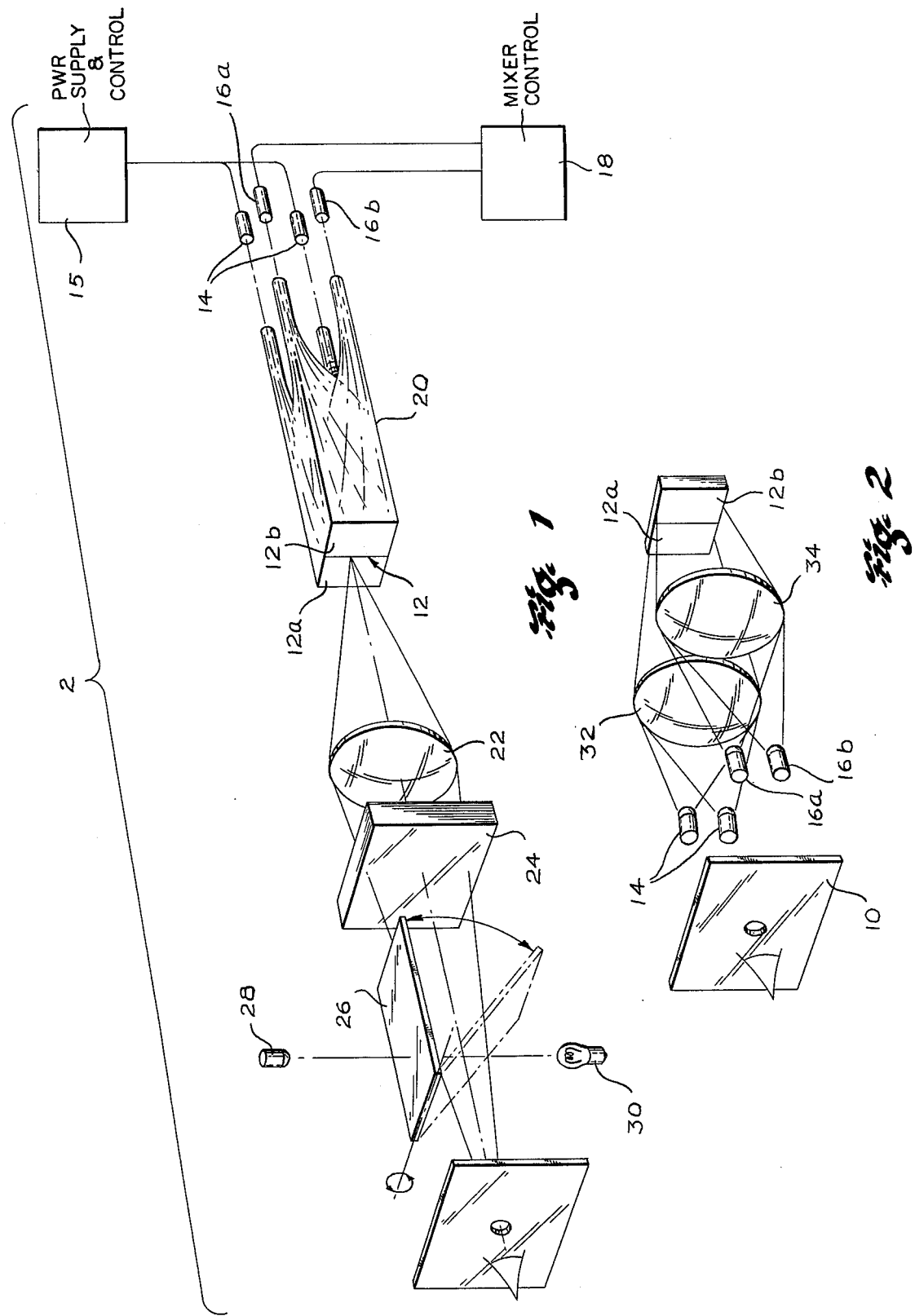

SOLID STATE COLOR ANOMALOSCOPE

BACKGROUND OF THE INVENTION

This invention relates to an instrument for identification of a color deficiency, for example, in a clinical environment. The instrument further identifies the nature of the color deficiency as well as the degree of its severity.

The instrument utilizes a color mixing technique wherein the patient attempts to match the fixed color of one half of a bi-partite field with the other half. This second half includes capacity for varying of hue by mixing together two colors in subjectively appropriate proportions.

The principle of the color anomaloscope finds its premise in the latter of two of Grassman's three laws:

2. If, of a two-component mixture, one component is steadily changed (while the other component is maintained constant), the color of the mixture steadily changes.

3. Lights of the same color (that is, of the same dominant wavelength, same luminance, and the same purity) produce identical effects in mixtures, regardless of their spectral composition.

Further reference to the 1931 CIE Chromaticity Diagram (a standard reference in the art) illustrates that any spectral color between 540 and 700 nm can be matched by a combination of appropriate proportions of the extremes of this range. The literature of the art shows that the proportions of the mixture in any color matching attempt, within the range, are the same for any normal observer. Those individuals which are deficient in color vision may be readily identified by observation of his variation from the norm.

The two types of color deficiencies which are frequently encountered in the human are deficiency of either the protans, or the deutans. The deficiency of protans will cause an individual to exhibit a deficiency of red-response, while the deficiency of deutans is evidenced in a sub-normal green-response. Each type of anomaly may range in severity from the characteristic of anomalous trichromatism to the more severe condition of severe dichromatism. An individual having the former deficiency demonstrates a three color response, however, either depressed in the green or red response and/or green or red wavelength limited. In the severe condition of dichromatism, the response to red or green is lacking.

The conditions of tritanism, or blue-blindness and the condition of monochromatism or total color-blindness, are so rare that the inclusion in a color anomaloscope of the ability to diagnose such a condition is not necessary. Rather, such inclusion would cause a clinical instrument to be overly complicated and expensive for normal commercial application since such extreme conditions are detectable by other suitable tests.

Prior art color anomaloscopes have employed incandescent sources, utilizing the likes of glass, gelatin or interference filters to develop luminescence of known spectral color. Monochromators and gas discharge tubes have also been employed as sources for such instruments. Unfortunately, such practical considerations as high cost, difficulty of control, extensive maintenance involvement, are associated with these prior embodiments of clinical instruments; and have suppressed the utilization (commercial production and sale) of such instruments for use in clinical testing and industrial screening.

There is a real need for a wavelength accurate color response measurer which may be operated by the professional or skilled technician which commands confidence that the measurements taken are indicative of patient characteristics. The present instrument utilizing precision light-emitting diodes offers these advantages.

SUMMARY OF THE INVENTION

A color anomaloscope for evaluating a human subject's color vision response so that color deficiencies may be identified. In accordance with certain features of the invention there is included light-emitting diode means for establishing a yellow color standard and, red and green light-emitting diode means for establishing an adjustable color mixture to be varied by the subject and matched to the standard. The instrument, in a preferred form, includes means for adjusting the luminance of the yellow diode and means for maintaining the total luminance of the red/green mixture constant, and in predetermined relation to the yellow luminance.

BRIEF DESCRIPTION OF THE DRAWINGS

The accompanying drawing shows by way of example only, certain embodiments of the invention.

FIG. 1 is a pictorial view of the elements of the invention.

FIG. 2 is a pictorial view of an alternative illuminator for the bi-partite fields of the invention.

DESCRIPTION OF A PREFERRED EMBODIMENT

Referring now to the figures, reference numeral 2 indicates the entirety of a color anomaloscope according to the present invention. The instrument may take the form of a hand-held tube containing the entirety of the operative elements.

As illustrated herein, the device may include an eyepiece 10 at one end, through which a patient may view a bipartite field 12. In field 12, one lateral half 12a is uniformly illuminated by a light-emitting diode (LED) 14, emitting at approximately 589 nm. This yellow LED is operated at a fixed emission level at a predetermined standard of illumination by luminance power supply and control 15.

The other lateral one-half of the bipartite field 12b is illuminated (uniformly) by two light-emitting diode sources, 16a, 16b in order to provide a color mixing technique whereby the patient may adjust, or direct the adjustment of, the output of LED sources 16a, 16b so as to "match" the yellow standard. In the illustrated embodiment, a red LED emitting at approximately 670 nm. is coupled through a mixer control 18 to a green LED emitting at approximately 540 nm. The mixer control 18 also operates to cause the total luminance output of diodes 16a, 16b to be constant over the entire useable mixture range.

Color mixing, by varying the proportions of the red and green emitting LED emissions, may be accomplished by a variety of approaches. For example, independent variable current controls may be employed with each of the LEDs 16a, 16b. Likewise, an independent variable pulse width (time) control, at a constant current level would be effective to control red-green mix for matching of fields 12.

It should be recognized that any one of a variety of optical schemes might be utilized to view the bipartite field 12. As illustrated in FIG. 1, a fiber optic mixer and coupler 20 is illustrated. The illustrated coupler provides a standard field 12a composed of the output of the yellow LED's 14 and the "matching" field 12b composed of the output of the red-green LED's 16a, 16b. By this scheme, the field 12 might be viewed through a lens 22 lying within the focal plane of lens 22 by the subject. It is important to here note that the optical scheme should provide an unresolvable view of the inputs 16a, 16b to form a complete mix such that this field (12b) may be directly compared (and thus resolved from) with field 12a.

Such other optical elements for satisfactory viewing may be included as an iris diaphragm 24 (for field control), a specular reflecting surface 26 (for calibration or white conditioning and appropriate detector 28 and light source 30 for such calibration and/or conditioning.

While the aforementioned fiber optic optical scheme has certain advantages for laboratory testing, it should be recognized that additional or other optical schemes may be advantageous for other circumstances. Reference to FIG. 2 illustrates a system wherein the output of LED's 14, 16a and 16b are projected upon such as an optical screen (e.g. white matte surface) to form the bipartite fields 12a, 12b. Such a system might include lenses 32, 34 to provide unresolvable mixing of the "matching" field 12b and clear resolution with the "standard" field 12a.

It is intended that the embodiments described herein be illustrative of the invention and that those modifications apparent to one skilled in the art be included within the scope of the invention.

For example, while prior art devices for observation of tritanism were necessarily complex, we consider adaptation of the present instrument for such observation to be a straight-forward, feasible modification. Presently, LEDs emitting in the blue color spectrum are not commercially available, so this described modification is not illustrated in the figures. Such inclusion is considered within the scope of the appended claims.

We claim:

1. Apparatus for evaluating a human subject's color vision response comprising: a light-emittion diode providing luminance in the yellow color spectrum; power means for driving said light-emitting diode and controlling said luminance; a light-emitting diode providing luminance in the red color spectrum; a light-emitting diode providing luminance in the green color spectrum; power means for driving said red and green light-emitting diodes; means for controlling said power means for said red and green diodes to cause the individual luminance of said diodes to be variably controlled in a predetermined inverse relationship; a display field; means for directing the luminance of said yellow diode on one portion of said display field; and means for directing a mixture of the luminance of said red and green diodes on an adjacent portion of said display field, whereby said human subject may observe and compare the displayed luminance of said yellow diode to said mixed luminance of said red and green diodes.

2. Apparatus according to claim 1 wherein said means for directing a mixture of said luminance of said red and green diodes is a fiber optic coupler having bipartite fields.

3. Apparatus according to claim 1 wherein said means for directing a mixture of said luminance of said red and green diodes includes lens means for imaging said luminance on an optical screen.

4. Apparatus according to claim 1 wherein said means for controlling said power means includes means to cause the total luminance of said red and green diodes to remain constant over the range of said variable predetermined inverse relationship.

* * * * *